United States Patent
Sundaresan et al.

(10) Patent No.: US 10,876,151 B2
(45) Date of Patent: Dec. 29, 2020

(54) LNA-BASED MUTANT ENRICHMENT NEXT-GENERATION SEQUENCING ASSAYS

(71) Applicant: The General Hospital Corporation, Boston, MA (US)

(72) Inventors: Tilak K. Sundaresan, Jamaica Plain, MA (US); Zongli Zheng, Hong Kong (CN); Daniel A. Haber, Chestnut Hill, MA (US); Shyamala Maheswaran, Lexington, MA (US); A. John Iafrate, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/566,116

(22) PCT Filed: Apr. 15, 2016

(86) PCT No.: PCT/US2016/027696
§ 371 (c)(1),
(2) Date: Oct. 12, 2017

(87) PCT Pub. No.: WO2016/168561
PCT Pub. Date: Oct. 20, 2016

(65) Prior Publication Data
US 2018/0112259 A1 Apr. 26, 2018

Related U.S. Application Data

(60) Provisional application No. 62/248,154, filed on Oct. 29, 2015, provisional application No. 62/147,851, filed on Apr. 15, 2015.

(51) Int. Cl.
*C12Q 1/68* (2018.01)
*C12N 15/10* (2006.01)
*C12Q 1/6827* (2018.01)

(52) U.S. Cl.
CPC ....... *C12Q 1/6827* (2013.01); *C12N 15/1058* (2013.01)

(58) Field of Classification Search
None
See application file for complete search history.

(56) References Cited

U.S. PATENT DOCUMENTS

| 2010/0227329 | A1 | 9/2010 | Cuppens |
| 2012/0225421 | A1* | 9/2012 | Richardson .......... C12Q 1/6869 435/5 |
| 2013/0303461 | A1 | 11/2013 | Iafrate et al. |

FOREIGN PATENT DOCUMENTS

| CA | 2886334 | 4/2014 |
| CN | 103517993 | 1/2014 |
| CN | 107604053 | 1/2018 |
| CN | 110546273 | 12/2019 |
| WO | WO 2007/106534 | 9/2007 |
| WO | WO 2012/151560 | 11/2012 |

OTHER PUBLICATIONS

Fadrosh DW, Ma B, Gajer P, Sengamalay N, Ott S, Brotman RM, Ravel J. An improved dual-indexing approach for multiplexed 16S rRNA gene sequencing on the Illumina MiSeq platform. Microbiome. Feb. 24, 2014; 2(1):6. (Year: 2014).*
Heitzer E, Ulz P, Geigl JB. Circulating tumor DNA as a liquid biopsy for cancer. Clin Chem. Jan. 2015; 61(1):112-23. Epub Nov. 11, 2014. (Year: 2015).*
Janku F, Vibat CR, Kosco K, Holley VR, Cabrilo G, Meric-Bernstam F, Stepanek VM, Lin PP, Leppin L, Hassaine L, Poole JC, Kurzrock R, Erlander MG. BRAF V600E mutations in urine and plasma cell-free DNA from patients with Erdheim-Chester disease. Oncotarget. Jun. 15, 2014; 5(11):3607-10. (Year: 2014).*
Tanaka et al. Reliability of the peptide nucleic acid-locked nucleic acid polymerase chain reaction clamp-based test for epidermal growth factor receptor mutations integrated into the clinical practice for non-small cell lung cancers. Cancer Sci. Feb. 2007; 98(2): 246-52. (Year: 2007).*
Oxnard et al. Noninvasive detection of response and resistance in EGFR-mutant lung cancer using quantitative next-generation genotyping of cell-free plasma DNA. Clin Cancer Res. Mar. 15, 2014; 20(6):1698-1705. Epub Jan. 15, 2014. (Year: 2014).*
Bentley et al. (2008) Supplementary Information. pp. 1-55. Nature. Nov. 6, 2008; 456(7218):53-9. (Year: 2008).*
Kukita Y, Uchida J, Oba S, Nishino K, Kumagai T, Taniguchi K, Okuyama T, Imamura F, Kato K. Quantitative identification of mutant alleles derived from lung cancer in plasma cell-free DNA via anomaly detection using deep sequencing data. PloS one. Nov. 21, 2013; 8(11):e81468. (Year: 2013).*
Kukita et al. Supplementary Table S5 (2013) PloS one. Nov. 21, 2013; 8(11):e81468: p. 1. (Year: 2013).*
Genbank Accession No. KJ891123.1-Synthetic construct *Homo sapiens* clone ccsbBroadEn_00517 ESR1 gene, encodes complete protein (submitted by May 28, 2014, retrieved on Mar. 4, 2019 from http://www.ncbi.nlm.nih.gov/nuccore/KJ891123). (Year: 2014).*
Peng Q, Vijaya Satya R, Lewis M, Randad P, Wang Y. Reducing amplification artifacts in high multiplex amplicon sequencing by using molecular barcodes. BMC Genomics. Aug. 7, 2015;16:589. (Year: 2015).*
Peng et al. Supporting information, BMC Genomics. Aug. 7, 2015;16:589: pp. 1-68. (Year: 2015).*
English translation of CN107604053, published Jan. 19, 2018 and recovered from espacenet on Nov 20, 2020,. (Year: 2018).*
English translation of CN110546273, published Dec. 6, 2019 and recovered from espacenet on Nov 20, 2020,. (Year: 2019).*

(Continued)

*Primary Examiner* — Teresa E Strzelecka
*Assistant Examiner* — Olayinka A Oyeyemi
(74) *Attorney, Agent, or Firm* — Fish & Richardson P.C.

(57) ABSTRACT

Ultra-sensitive assays for the detection of mutations, e.g., from blood-based sources of tumor genetic material (circulating tumor cells or plasma), or other settings in which limiting amounts of DNA, e.g., tumor DNA, is available. The assay is exemplified in the estrogen receptor, but is broadly customizable to target mutations in other genes.

12 Claims, 5 Drawing Sheets

Specification includes a Sequence Listing.

(56) References Cited

OTHER PUBLICATIONS

International Search Report and Written Opinion dated Aug. 23, 2016 in international application No. PCT/US2016/027696, 12 pgs.
Bybee et al., "Directed next generation sequencing for phylogenetics: An example using Decapoda (Crustacea)," Zoologischer Anzeiger, May 2011, 250: 497-506.
Extended European Search Report in Application No. 16780809.6, dated Aug. 13, 2018, 9 pages.
Guha et al., "Dissect Method Using PNA-LNA Clamp Improves Detection of EGFR T790m Mutation," PLOS ONE, Jun. 2013, 8: e67782.
Kim et al., "Predictive Efficacy of Low Burden EGFR Mutation Detected by Next-Generation Sequencing on Response to EGFR Tyrosine Kinase Inhibitors in Non-Small-Cell Lung Carcinoma," PLOS ONE, Dec. 2013, 3: e81975.
Lin et al., "Abstract 1506: Mutant enrichment by ICE COLD-PCR prior to the next-generation sequencing enables high sensitivity and high throughput detection of cancer biomarkers in patient samples," Proceedings of the 105th Annual Meeting of the American Association for Cancer Research, Oct. 2014, 74(19 Suppl): 5 pages.
Arcila et al., "Rebiopsy of Lung Cancer Patients with Acquired Resistance to EGFR Inhibitors and Enhanced Detection of the T790M Mutation Using a Locked Nucleic Acid-Based Assay," Clinical Cancer Research, Mar. 2011, 17: 1170-1180.
Burstein et al., "Adjuvant Endocrine Therapy for Women With Hormone Receptor-Positive Breast Cancer: American Society of Clinical Oncology Clinical Practice Guideline Focused Update," J Clin Oncol, Jul. 2014;32(21):2255-2269.
International Preliminary Report on Patentability in International Application No. PCT/US2016/027696, dated Oct. 17, 2017, 6 pages.
Jepsen et al., "Locked nucleic acid: a potent nucleic acid analog in therapeutics and biotechnology," Oligonucleotides, 2004, 14: 130-146.
Jeselsohn et al., "Emergence of constitutively active estrogen receptor-alpha mutations in pretreated advanced estrogen receptor-positive breast cancer," Clinical Cancer Research, 2014, 20:1757-67.
Jeselsohn et al., "ESR1 mutations—a mechanism for acquired endocrine resistance in breast cancer," Nat Rev Clin Oncol, Oct. 2015, 12(10):573-83.
Li et al., "Endocrine-therapy-resistant ESR1 variants revealed by genomic characterization of breast-cancer-derived xenografts," Cell Reports, 2013, 4:1116-30.
Lumachi et al., "Endocrine Therapy of Breast Cancer," Curr Med Chem, 2011, 18(4):513-22.
Majewski et al., "PIK3CA mutations are associated with decreased benefit to neoadjuvant human epidermal growth factor receptor 2-targeted therapies in breast cancer," J Clin Oncol, Apr. 2015, 33(12):1334-1339.
Robinson et al., "Activating ESR1 mutations in hormone-resistant metastatic breast cancer," Nature Genetics, 2013, 45:1446-51.
Segal and Dowsett, "Estrogen Receptor Mutations in Breast Cancer—New Focus on an Old Target," Clin Cancer Res, Apr. 2014, 20:1724-1726.
Toy et al., "ESR1 ligand-binding domain mutations in hormone-resistant breast cancer," Nature Genetics, Dec. 2013, 45:1439-45.
You et al., "Design of LNA probes that improve mismatch discrimination," Nucleic Acids Research, 2006, 34: e60.
Yu et al., "Cancer therapy. Ex vivo culture of circulating breast tumor cells for individualized testing of drug susceptibility," Science, Jul. 2014, 345:216-20.
EP Office Action in European Appln. No. 16780809.6, dated Apr. 28, 2020, 5 pages.
EP Office Action in European Appln. No. 16780809.6, dated Aug. 23, 2019, 4 pages.
CN Office Action in Chinese Appln. No. 201680022209.5, dated Aug. 5, 2020, 12 pages (with English translation).
CN Search Report in Chinese Appln. No. 201680022209.5, dated Jul. 29, 2020, 4 pages.
Guohui, "Application of next-generation sequencing technology in lymphoma," Journal of Clinical Blood, Mar. 2014, 27(11):931-935, (16 pages with English language Machine Translation).
Guttery et al., "Noninvasive detection of activating estrogen receptor 1 (ESR1) mutations in estrogen receptor—positive metastatic breast cancer," Clinical Chemistry, Jul. 2015, 61(7):974-982.
Jun et al., "Application of next-generation sequencing technologies in molecular diagnostics," Journal of Molecular Diagnosis and Therapy, May 2013, 5(3):145-151, (7 pages with English abstract).

* cited by examiner

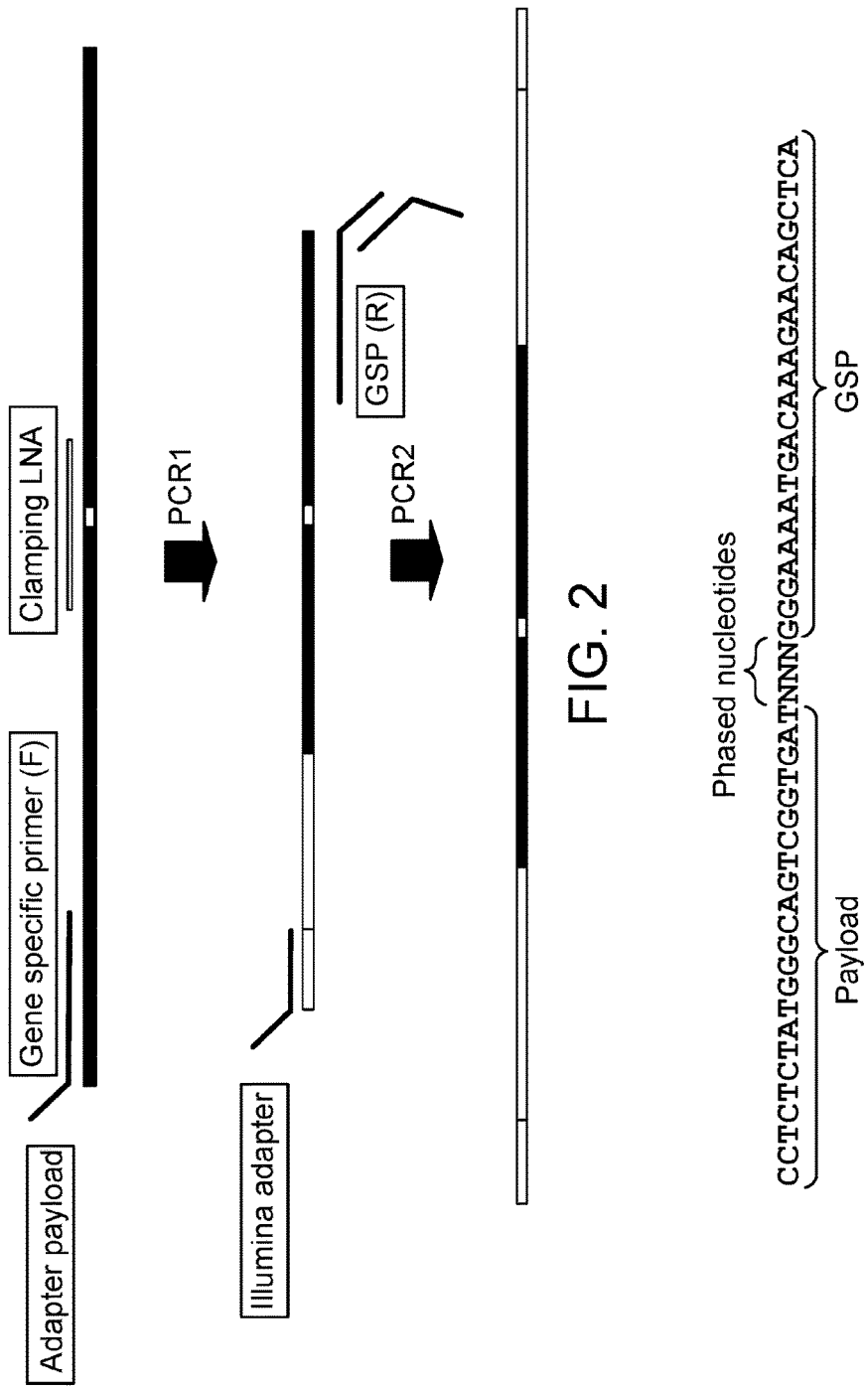

| Sample ID | ESR1 Genotype |
|---|---|
| BR29 | WT |
| BRx 114 | WT |
| BRx 116 | Y537S |
| BRx 117 | Y537S |
| BRx 122 | WT |
| BRx 124 | WT |
| BRx 126 | WT |
| BRx 134 | WT |
| BRx 135 | WT |
| BRx 140 | WT |
| BRx 146 | Y537N / Y537S |
| BRx 149 | WT |
| BRx 150 | Silent mut |
| BRx 168 | WT |
| BRx 173 | Y537S |
| BRx 175 | WT |
| BRx 178 | Silent mut |
| BRx 186 | WT |
| BRx 187 | Y537S / D538G |
| BRx 190 | WT |
| BRx 29 | L536Q |
| BRx 55 | L536I |
| BRx 70 | Y537S |
| BRx 78 | WT |
| BRx 90 | WT |

FIG. 6

```
                        SEQUENCE LISTING

<160> NUMBER OF SEQ ID NOS: 86

<210> SEQ ID NO 1
<211> LENGTH: 20
<212> TYPE: DNA
<213> ORGANISM: Homo sapiens

<400> SEQUENCE: 1
tgccactcta tgacctgctg                                               20

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: a, c, t, g, unknown or other

<400> SEQUENCE: 2
tctttcccta cacgacgctc ttccgatctn tccattttag cacttacctg tgac         54

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other
```

<400> SEQUENCE: 3
cctctctatg ggcagtcggt gatngggaaa atgacaaaga acagctca        48

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: a, c, t, g, unknown or other

<400> SEQUENCE: 4
tctttcccta cacgacgctc ttccgatctn accctagcct tagataaaac tgagca       56

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other

<400> SEQUENCE: 5
cctctctatg ggcagtcggt gatntgcatg ctgtttaatt gtgtggaag       49

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: a, c, t, g, unknown or other

<400> SEQUENCE: 6
tctttcccta cacgacgctc ttccgatctn tcccacctac agtaacaaag gcatgg       56

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other

<400> SEQUENCE: 7
cctctctatg ggcagtcggt gatnggctag tgggcgcatg taggc       45

<210> SEQ ID NO 8
<211> LENGTH: 20
<212> TYPE: DNA
<213> ORGANISM: Homo sapiens

<400> SEQUENCE: 8
tctcctgctc agtgatttca                                                      20

<210> SEQ ID NO 9
<211> LENGTH: 20
<212> TYPE: DNA
<213> ORGANISM: Homo sapiens

<400> SEQUENCE: 9
tgcacatcat ggtggctgga                                                      20

<210> SEQ ID NO 10
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 10
aatgatacgg cgaccaccga gatctacacc gtaggtannw nnwnnacact ctttccctac          60
acgacgctct tccgatct                                                        78

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 11
aatgatacgg cgaccaccga gatctacaca gctagcgnnw nnwnnacact ctttccctac          60
acgacgctct tccgatct                                                        78

<210> SEQ ID NO 12
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 12
aatgatacgg cgaccaccga gatctacact cctgtgcnnw nnwnnacact ctttccctac    60
acgacgctct tccgatct                                                 78

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 13
aatgatacgg cgaccaccga gatctacacg taatctgnnw nnwnnacact ctttccctac    60
acgacgctct tccgatct                                                 78

<210> SEQ ID NO 14
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 14
aatgatacgg cgaccaccga gatctacaca acgtaggnnw nnwnnacact ctttccctac    60
acgacgctct tccgatct                                                 78

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 15
aatgatacgg cgaccaccga gatctacact tcctgttnnw nnwnnacact ctttccctac      60
acgacgctct tccgatct                                                   78

<210> SEQ ID NO 16
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 16
aatgatacgg cgaccaccga gatctacact gtccagtnnw nnwnnacact ctttccctac      60
acgacgctct tccgatct                                                   78

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 17
aatgatacgg cgaccaccga gatctacaca caaggcannw nnwnnacact ctttccctac      60
acgacgctct tccgatct                                                   78

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 18
aatgatacgg cgaccaccga gatctacacc cttgaccnnw nnwnnacact ctttccctac      60
acgacgctct tccgatct                                                   78

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 19
aatgatacgg cgaccaccga gatctacacc gcttgtgnnw nnwnnacact ctttccctac      60
acgacgctct tccgatct                                                   78

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 20
aatgatacgg cgaccaccga gatctacact ccaagcgnnw nnwnnacact ctttccctac      60
acgacgctct tccgatct                                                   78

<210> SEQ ID NO 21
<211> LENGTH: 78
<212> TYPE: DNA
<213> ORGANISM: Artificial Sequence
<220> FEATURE:
```

<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 21
aatgatacgg cgaccaccga gatctacacc tagtgacnnw nnwnnacact ctttccctac      60
acgacgctct tccgatct                                                   78

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 22
aatgatacgg cgaccaccga gatctacaca gaaccgtnnw nnwnnacact ctttccctac      60
acgacgctct tccgatct                                                   78

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 23
aatgatacgg cgaccaccga gatctacact aattgcannw nnwnnacact ctttccctac      60
acgacgctct tccgatct                                                   78

<210> SEQ ID NO 24
<211> LENGTH: 78
<212> TYPE: DNA

<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 24
aatgatacgg cgaccaccga gatctacacc tagtacannw nnwnnacact ctttccctac    60
acgacgctct tccgatct                                                  78

<210> SEQ ID NO 25
<211> LENGTH: 78
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 25
aatgatacgg cgaccaccga gatctacacg ctatatcnnw nnwnnacact ctttccctac    60
acgacgctct tccgatct                                                  78

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 26
aatgatacgg cgaccaccga gatctacacc aatcggcnnw nnwnnacact ctttccctac    60
acgacgctct tccgatct                                                  78

<210> SEQ ID NO 27

```
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 27
aatgatacgg cgaccaccga gatctacacc gatatcannw nnwnnacact ctttccctac    60
acgacgctct tccgatct                                                 78

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 28
aatgatacgg cgaccaccga gatctacacc agtcaggnnw nnwnnacact ctttccctac    60
acgacgctct tccgatct                                                 78

<210> SEQ ID NO 29
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 29
aatgatacgg cgaccaccga gatctacacg taataatnnw nnwnnacact ctttccctac    60
acgacgctct tccgatct                                                 78
```

```
<210> SEQ ID NO 30
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 30
aatgatacgg cgaccaccga gatctacacg gagagatnnw nnwnnacact ctttccctac    60
acgacgctct tccgatct                                                 78

<210> SEQ ID NO 31
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 31
aatgatacgg cgaccaccga gatctacacc tctcatannw nnwnnacact ctttccctac    60
acgacgctct tccgatct                                                 78

<210> SEQ ID NO 32
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 32
aatgatacgg cgaccaccga gatctacacc agcgactnnw nnwnnacact ctttccctac    60
```
acgacgctct tccgatct                                                        78

<210> SEQ ID NO 33
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 33
aatgatacgg cgaccaccga gatctacacg gccaaggnnw nnwnnacact ctttccctac        60
acgacgctct tccgatct                                                        78

<210> SEQ ID NO 34
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 34
aatgatacgg cgaccaccga gatctacacg catatgcnnw nnwnnacact ctttccctac        60
acgacgctct tccgatct                                                        78

<210> SEQ ID NO 35
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 35

```
aatgatacgg cgaccaccga gatctacaca ctaggatnnw nnwnnacact ctttccctac    60
acgacgctct tccgatct                                                 78
```

<210> SEQ ID NO 36
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 36

```
aatgatacgg cgaccaccga gatctacacc cttacctnnw nnwnnacact ctttccctac    60
acgacgctct tccgatct                                                 78
```

<210> SEQ ID NO 37
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 37

```
aatgatacgg cgaccaccga gatctacact gttgacgnnw nnwnnacact ctttccctac    60
acgacgctct tccgatct                                                 78
```

<210> SEQ ID NO 38
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

```
<400> SEQUENCE: 38
aatgatacgg cgaccaccga gatctacact acagttannw nnwnnacact ctttccctac    60
acgacgctct tccgatct                                                  78

<210> SEQ ID NO 39
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 39
aatgatacgg cgaccaccga gatctacact tgttacgnnw nnwnnacact ctttccctac    60
acgacgctct tccgatct                                                  78

<210> SEQ ID NO 40
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 40
aatgatacgg cgaccaccga gatctacact cgtgttgnnw nnwnnacact ctttccctac    60
acgacgctct tccgatct                                                  78

<210> SEQ ID NO 41
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
```

<223> OTHER INFORMATION: a, c, t, g, unknown or other

<400> SEQUENCE: 41
aatgatacgg cgaccaccga gatctacaca gtcaatgnnw nnwnnacact ctttccctac    60
acgacgctct tccgatct                                                 78

<210> SEQ ID NO 42
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 42
aatgatacgg cgaccaccga gatctacact ctgtagannw nnwnnacact ctttccctac    60
acgacgctct tccgatct                                                 78

<210> SEQ ID NO 43
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 43
aatgatacgg cgaccaccga gatctacacg acaacgannw nnwnnacact ctttccctac    60
acgacgctct tccgatct                                                 78

<210> SEQ ID NO 44
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:

```
<221> NAME/KEY: modified_base
<222> LOCATION: (44)..(45)
<223> OTHER INFORMATION: a, c, t, g, unknown or other

<400> SEQUENCE: 44
aatgatacgg cgaccaccga gatctacacc catggctnnw nnwnnacact ctttccctac    60
acgacgctct tccgatct                                                  78

<210> SEQ ID NO 45
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 45
aatgatacgg cgaccaccga gatctacact gactctgnnw nnwnnacact ctttccctac    60
acgacgctct tccgatct                                                  78

<210> SEQ ID NO 46
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 46
aatgatacgg cgaccaccga gatctacaca acgaggcnnw nnwnnacact ctttccctac    60
acgacgctct tccgatct                                                  78

<210> SEQ ID NO 47
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
```

<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 47
aatgatacgg cgaccaccga gatctacacc agaaggtnnw nnwnnacact ctttccctac    60
acgacgctct tccgatct                                                  78

<210> SEQ ID NO 48
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 48
aatgatacgg cgaccaccga gatctacact gaagtcannw nnwnnacact ctttccctac    60
acgacgctct tccgatct                                                  78

<210> SEQ ID NO 49
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 49
aatgatacgg cgaccaccga gatctacaca tgttcctnnw nnwnnacact ctttccctac    60
acgacgctct tccgatct                                                  78

<210> SEQ ID NO 50
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:

```
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 50
aatgatacgg cgaccaccga gatctacaca agtggctnnw nnwnnacact ctttccctac    60
acgacgctct tccgatct                                                 78

<210> SEQ ID NO 51
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 51
aatgatacgg cgaccaccga gatctacacg gtacaatnnw nnwnnacact ctttccctac    60
acgacgctct tccgatct                                                 78

<210> SEQ ID NO 52
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 52
aatgatacgg cgaccaccga gatctacaca caagtgcnnw nnwnnacact ctttccctac    60
acgacgctct tccgatct                                                 78

<210> SEQ ID NO 53
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
```

<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 53
aatgatacgg cgaccaccga gatctacact cacggtgnnw nnwnnacact ctttccctac    60
acgacgctct tccgatct                                                  78

<210> SEQ ID NO 54
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 54
aatgatacgg cgaccaccga gatctacact tgcgttannw nnwnnacact ctttccctac    60
acgacgctct tccgatct                                                  78

<210> SEQ ID NO 55
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 55
aatgatacgg cgaccaccga gatctacact tgtagccnnw nnwnnacact ctttccctac    60
acgacgctct tccgatct                                                  78

<210> SEQ ID NO 56
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 56
aatgatacgg cgaccaccga gatctacact caccggannw nnwnnacact ctttccctac    60
acgacgctct tccgatct                                                  78

<210> SEQ ID NO 57
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 57
aatgatacgg cgaccaccga gatctacacc gcgcaagnnw nnwnnacact ctttccctac    60
acgacgctct tccgatct                                                  78

<210> SEQ ID NO 58
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caagcagaag acggcatacg agattcgcct tagtgactgg agtcctctct atgggcagtc    60
ggtga                                                                65

<210> SEQ ID NO 59
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
caagcagaag acggcatacg agatctagta cggtgactgg agtcctctct atgggcagtc    60
ggtga                                                                65

<210> SEQ ID NO 60
<211> LENGTH: 65
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 60
caagcagaag acggcatacg agatttctgc ctgtgactgg agtcctctct atgggcagtc    60
ggtga                                                                65

<210> SEQ ID NO 61
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
caagcagaag acggcatacg agatgctcag gagtgactgg agtcctctct atgggcagtc    60
ggtga                                                                65

<210> SEQ ID NO 62
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
caagcagaag acggcatacg agataggagt ccgtgactgg agtcctctct atgggcagtc    60
ggtga                                                                65

<210> SEQ ID NO 63
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
caagcagaag acggcatacg agatcatgcc tagtgactgg agtcctctct atgggcagtc    60
ggtga                                                                65

<210> SEQ ID NO 64
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
caagcagaag acggcatacg agatgtagag aggtgactgg agtcctctct atgggcagtc    60
ggtga                                                                65

<210> SEQ ID NO 65
<211> LENGTH: 65
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 65
caagcagaag acggcatacg agatcctctc tggtgactgg agtcctctct atgggcagtc    60
ggtga                                                               65

<210> SEQ ID NO 66
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caagcagaag acggcatacg agatagcgta gcgtgactgg agtcctctct atgggcagtc    60
ggtga                                                               65

<210> SEQ ID NO 67
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caagcagaag acggcatacg agatcagcct cggtgactgg agtcctctct atgggcagtc    60
ggtga                                                               65

<210> SEQ ID NO 68
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caagcagaag acggcatacg agattgcctc ttgtgactgg agtcctctct atgggcagtc    60
ggtga                                                               65

<210> SEQ ID NO 69
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
caagcagaag acggcatacg agattcctct acgtgactgg agtcctctct atgggcagtc    60
ggtga                                                               65

<210> SEQ ID NO 70
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caagcagaag acggcatacg agataacttc acgtgactgg agtcctctct atgggcagtc    60
``` ggtga                                                              65

<210> SEQ ID NO 71
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caagcagaag acggcatacg agattggaga gggtgactgg agtcctctct atgggcagtc    60
ggtga                                                              65

<210> SEQ ID NO 72
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caagcagaag acggcatacg agatacgcat cggtgactgg agtcctctct atgggcagtc    60
ggtga                                                              65

<210> SEQ ID NO 73
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caagcagaag acggcatacg agatgtaccg ttgtgactgg agtcctctct atgggcagtc    60
ggtga                                                              65

<210> SEQ ID NO 74
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caagcagaag acggcatacg agattacagt tagtgactgg agtcctctct atgggcagtc    60
ggtga                                                              65

<210> SEQ ID NO 75
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
caagcagaag acggcatacg agataaatcaa ctgtgactgg agtcctctct atgggcagtc   60
ggtga                                                              65

```
<210> SEQ ID NO 76
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caagcagaag acggcatacg agatgtacct aggtgactgg agtcctctct atgggcagtc      60
ggtga                                                                  65

<210> SEQ ID NO 77
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caagcagaag acggcatacg agatctggaa cagtgactgg agtcctctct atgggcagtc      60
ggtga                                                                  65

<210> SEQ ID NO 78
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caagcagaag acggcatacg agatggtgac tagtgactgg agtcctctct atgggcagtc      60
ggtga                                                                  65

<210> SEQ ID NO 79
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
caagcagaag acggcatacg agatgtgcaa ccgtgactgg agtcctctct atgggcagtc      60
ggtga                                                                  65

<210> SEQ ID NO 80
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
caagcagaag acggcatacg agatgcctgt ctgtgactgg agtcctctct atgggcagtc      60
ggtga                                                                  65

<210> SEQ ID NO 81
<211> LENGTH: 65
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 81
caagcagaag acggcatacg agatactgat gggtgactgg agtcctctct atgggcagtc      60
ggtga                                                                 65

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aatgatacgg cgaccaccga                                                 20

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(26)
<223> OTHER INFORMATION: a, c, t, g, unknown or other

<400> SEQUENCE: 83
cctctctatg ggcagtcggt gatnnnggga aaatgacaaa gaacagctca                50

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tctcctgctc agtgatttca t                                               21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgcacatcat ggtggctgga t                                               21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgcccctcta tgacctgctg t                                               21
```

LNA-BASED MUTANT ENRICHMENT NEXT-GENERATION SEQUENCING ASSAYS

CLAIM OF PRIORITY

This application is a U.S. National Phase Application under 35 U.S.C. § 371 of International Patent Application No. PCT/US2016/027696, filed on Apr. 15, 2016, which claims the benefit of U.S. Provisional Patent Application Ser. Nos. 62/147,851, filed Apr. 15, 2015, and 62/248,154, filed on Oct. 29, 2015. The entire contents of the foregoing are hereby incorporated by reference.

FEDERALLY SPONSORED RESEARCH OR DEVELOPMENT

This invention was made with Government support under Grant No. CA129933 awarded by the National Institutes of Health. The Government has certain rights in the invention.

TECHNICAL FIELD

Described are ultra-sensitive PCR-based assays for the detection of mutations, e.g., from blood-based sources of tumor genetic material (circulating tumor cells or plasma), or other settings in which limiting amounts of DNA, e.g., tumor DNA, is available.

BACKGROUND

Analysis of tumor-derived genetic material from non-tissue based sources is poised to revolutionize the management of cancer. Numerous sources of such tumor-derived DNA exist, including but not limited to circulating tumor DNA in plasma and urine (ctDNA), circulating tumor cells (CTCs), and exosomes. The detection of tumor-specific mutations from all of these sources, however, is complicated by their exceptional rarity in a background of normal cellular DNA.

SUMMARY

Previous methods for mutation detection from noninvasive sources of tumor DNA are limited by insufficient sensitivity and cost. Described herein is a new approach, known as Enrich-Seq, to address these shortcomings. The method enlists mutant enrichment using a locked-nucleic acid clamp in combination with a novel technique for library preparation that can accommodate a wide range of input DNA. A highly stringent, multi-phase bioinformatics approach is then applied to ensure optimal specificity of mutation calling.

Thus, provided herein are methods for detecting mutations in a target sequence of a double stranded DNA molecule (dsDNA). The methods include providing a sample comprising the dsDNA; contacting the sample with:

a forward gene-specific primer comprising a first hemi-functional NGS adapter sequence, and a clamping oligonucleotide that optionally comprises one or more locked nucleotides, wherein the forward primer and clamping oligonucleotide are in cis, and wherein the clamping oligo hybridizes to a wild type sequence of the target gene in a region suspected of comprising one or more mutations;

performing a first round of single strand primer extension PCR, to produce a first population of amplicons;
optionally purifying the first population of amplicons;
contacting the first population of amplicons with:
a first universal primer complementary to a portion of the first hemi-functional NGS adapter sequence, wherein amplification with the primer creates a first fully functional NGS adapter sequence,
a reverse gene specific primer comprising a second hemi-functional NGS adapter sequence, wherein the reverse primer is in trans with the primer complementary to a portion of the first NGS adapter sequence, and;
a second universal primer identical to the second hemi-functional NGS adapter sequence on the reverse primer, wherein amplification with the second universal primer creates a second fully functional NGS adapter sequence;
performing a second round of PCR ("PCR2") to complete amplification of a second population of amplicons comprising both first and second fully functional NGS adapter sequences; sequencing the second population of amplicons; and
comparing the sequences of the second population of amplicons to a reference wild typo target sequence;
to thereby detect mutations (differences from the wild-type sequence) in the target sequence.

In some embodiments, the dsDNA is or comprises genomic DNA. In some embodiments, the dsDNA is from circulating tumor DNA (ctDNA), e.g., in plasma or urine, circulating tumor cells (CTCs), or exosomes.

In some embodiments, purifying the first population of amplicons comprises using solid-phase reversible immobilization (SPRI) bead-based cleanup, In some embodiments, the target sequence is in the estrogen receptor 1 (ESR1), e.g., in the ligand binding domain, e.g., ESR1 wild type sequence TGCCCCTC-TATGACCTGCTG (SEQ ID NO:1). Mutations in ESR1 can include, e.g., V534E (1601T>A), P535H (1604C>A), L536R/P/Q (1607T>G/1607T>C/1607TC>AG), Y537N/C/S (1609T>A/1610A>G/1610A>C), or D538G (1613A>G). In some embodiments, the methods include identifying a subject who has a mutation in ESR1 as having or at risk of developing estrogen receptor (ER)-positive breast cancer that is resistant to endocrine therapy. In some embodiments, the methods include identifying a subject who has a mutation in ESR1 as unlikely to respond to treatment with endocrine therapy. In some embodiments, the methods include selecting and optionally administering a therapy that does not include endocrine therapy to a subject who has been identified as having a mutation in ESR1; therapeutic options can include treating the subject with chemotherapy or endocrine therapy plus molecular-targeted therapy such as everolimus (Afinitor) or palbociclib (Ibrance). The methods can also include predicting response to treatment with endocrine therapy including investigational agents such as next generation estrogen receptor degraders, combination therapy using endocrine therapy plus histone deacetylase inhibitors, PI3K pathway inhibitors, or androgen receptor blockers.

In some embodiments, the target sequence is in phosphatidylinositol-4,5-bisphosphate 3-kinase, catalytic subunit alpha (PIK3CA), e.g., in exons 9 and/or 20, e.g., comprises PIK3CA Exon 9 wild type sequence: TCTCCTGCTCAGT-GATTTCA (SEQ ID NO:8) or PIK3CA Exon 20 wild type sequence: TGCACATCATGGTGGCTGGA (SEQ ID NO:9). Mutations in PIK3CA can include, e.g., E542K (c.1624G→A), E545K/Q/G/V (c.1633G→A/1633G>C/1634A>G/1634A>T. In some embodiments, the methods include identifying a subject who has a mutation in PIK3CA as having or at risk of developing estrogen receptor (ER)-positive breast cancer that is non-responsive to treatment with trastuzumab and/or lapatinib. In some embodiments, the methods include identifying a subject who has a mutation in PIK3CA as unlikely to respond to treatment with trastuzumab and/or lapatinib. In some embodiments, the methods include selecting and optionally administering a therapy that does not include trastuzumab and/or lapatinib to a subject who has been identified as having a mutation in PIK3CA. The methods can also include predicting response to investigational therapy with PI3K/AKT pathway inhibitors.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2. Exemplary Enrich-Seq next-generation sequencing library preparation schematic. In PCR1, a gene-specific primer in cis with the clamping LNA sequence is used for single strand primer extension. The gene-specific primer also contains a hemi-functional NGS adapter payload. Following solid-phase reversible immobilization (SPRI) bead-based cleanup of the PCR1 product, a second round of PCR is completed using a first universal primer complementary to a portion of the adapter payload and a paired gene specific reverse primer on the opposite strand containing another hemi-functional NGS adapter payload. A second universal primer identical to the adapter payload on the reverse primer is used to complete amplification of fully indexed amplicons.

FIG. 3. Random phased oligomer. Gene-specific amplification primer with a phased 3 nucleotide random oligomer (SEQ ID NO:83).

FIG. 6. CTC ESR1 genotyping. ESR1 Enrich-Seq was piloted in an initial cohort of 25 women with metastatic breast cancer exposed to >2 lines of prior endocrine therapy. An ESR1 mutation was detected in 8/25 (32%) patients. In 10 patients with CTC ESR1 genotyping completed at multiple time points (bold), the genotype was consistent in 8/10. In two patients, two synchronous ESR1 mutations were detected.

DETAILED DESCRIPTION

Figure 1:
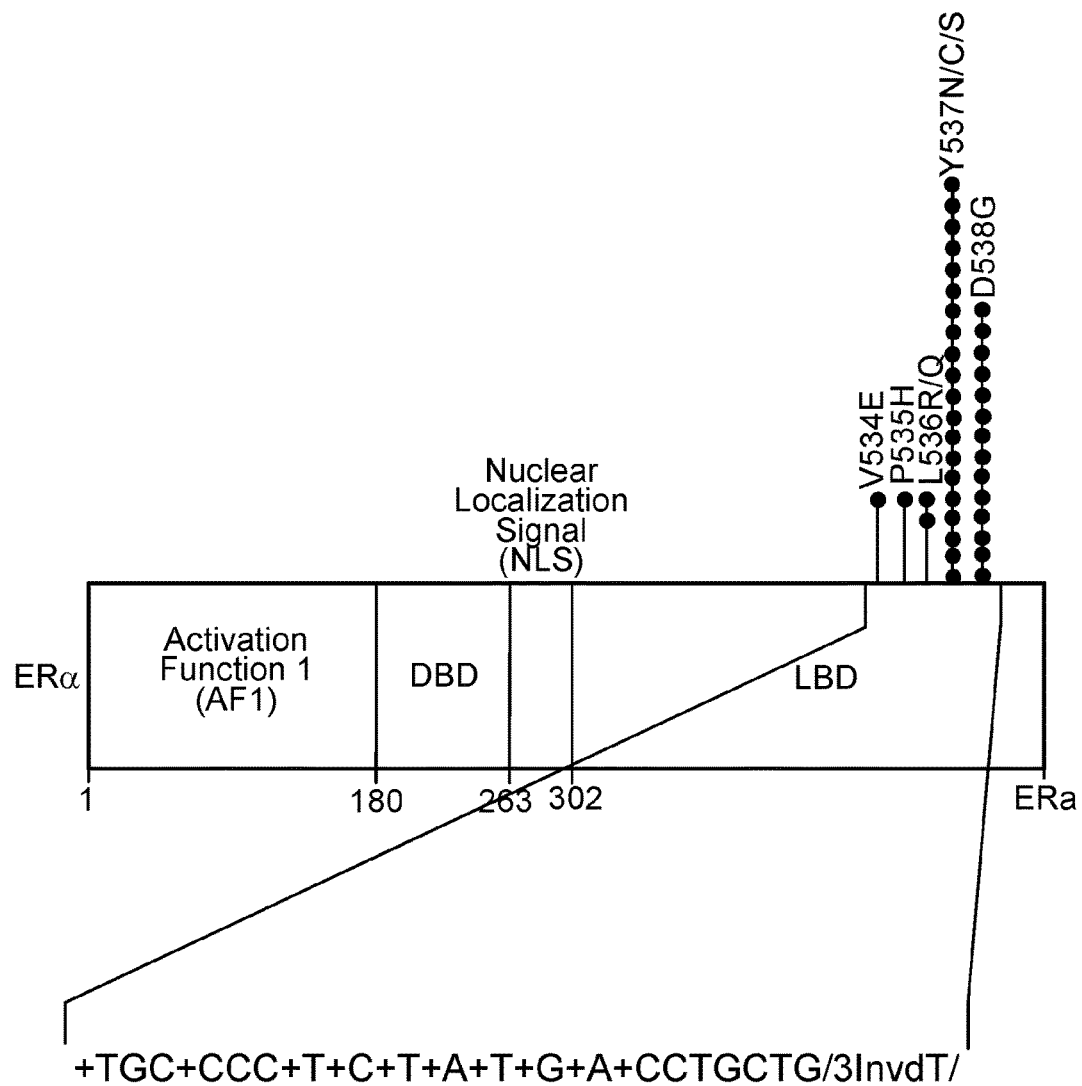
FIG. 1. Locked nucleic acid clamp sequence. An exemplary locked nucleic acid clamp (having the primary sequence of SEQ ID NO: 86) designed to span canonical estrogen receptor 1 (ESRI) ligand binding domain mutations. (Adapted in part from FIG. 1 of Segal and Dowsett, Clin Cancer Res Apr. 1, 2014 20: 1724-1726). In this figure the locked nucleotides are those following the + sign.

Mutations in the ligand-binding domain (LBD) of the estrogen receptor have recently been found in breast cancer samples from patients who have been treated with anti-estrogen therapy. In pre-clinical studies, these mutations have been observed to confer relative resistance to aromatase inhibitors as well as selective estrogen receptor modulators and estrogen receptor antagonists. This has led to increasing clinical interest in these mutations as a biomarker of acquired resistance to endocrine therapy.

The ability to non-invasively detect the presence of estrogen receptor mutations through blood-based sampling would permit serial monitoring for the emergence of acquired resistance and provide a comprehensive sampling of the entire malignant burden. Circulating tumor cells (CTC) and plasma circulating tumor DNA (ctDNA) provide tumor-derived genetic material that can be non-invasively obtained from patients but are both complicated by a large background of genetic material derived from normal cells.

Described herein is an ultra-sensitive method to detect mutations, such as estrogen receptor mutations, in both CTC and ctDNA. The technique utilizes mutant enrichment with unique locked nucleic acid sequences designed to detect multiple ESR1 ligand-binding mutations in a single assay. This allows us to parse rare mutant alleles from a large wild-type background. The mutant enrichment is combined with an innovative next-generation sequencing library preparation method that improves assay sensitivity while also allowing direct sequence confirmation of detected mutations to ensure higher assay specificity than seen in commercial allele specific assays or other mutant enrichment-based techniques. The inherent flexibility of the protocol also allows the straightforward adaptation of the assay to mutations in alternative genes.

This technology enables the real-time, non-invasive detection of mutations, e.g., estrogen receptor mutations, in patients, e.g., patients who are being treated with anti-estrogen therapy and may predict the emergence of treatment resistance, thereby guiding the selection of future therapy. In addition, the presence of an ESR1 mutation may warrant evaluation as a clinical biomarker to predict response to treatment, e.g., treatment with endocrine therapy including next generation estrogen receptor degraders.

Hemi-Functional Gene-Specific Primers

The methods described herein include the use of two-step PCR in which two rounds of PCR are conducted using Hemi-Functional gene-specific primers and Hemi-Functional sequencing primers. The gene-specific primers are referred to herein as "forward" and "reverse," which is indicative of the fact that they bind to opposing strands, but the "forward" primer can bind to either the sense or anti-sense strand (and "reverse" binds to the opposite strand). The gene-specific primers are designed to amplify a specific region that is known or suspected to comprise at least one mutation. The forward primer includes a hemi-functional next generation sequencing (NGS) adapter "payload"

sequence that can be used to attach an NGS primer, e.g., for use with an Illumina or IonTorrent sequencing platform. The reverse primer, which as noted above is in trans with the forward primer, also contains a hemi-functional NGS adapter "payload" sequence. The hemi-functional gene specific primers can be designed for any gene target and to accommodate any NGS platform, e.g., on MiSeq (Illumina) or Ion Torrent (Life Technologies) platforms. Hemi-functional gene-specific primers for use in amplifying mutations in ESR1 or phosphatidylinositol-4,5-bisphosphate 3-kinase, catalytic subunit alpha (PIK3CA) can include those described herein.

The universal hemi-functional sequencing primers have a variable sequence that includes two halves—one half that is consistent across all of the primers used for a given gene that is complementary to the "payload" sequence on the hemi-functional GSP, and another half that includes the NGS adapter sequence. There are hundreds of these latter sequences, e.g., the MiSeq sequences published by Illumina, allowing the indexing of multiple samples in a single reaction.

Clamp Oligonucleotides

Clamping oligos can be made for hotspot mutations in any gene, though differential hybridization and resulting relative mutant enrichment may differ based on the genetic context. The length and annealing temperature of the clamp should be optimized using methods known in the art (see, e.g., You et al., Nucleic Acids Research, 2006, Vol. 34, No. 8 e60) to permit the greatest mismatch discrimination between hybridization to wild-type and mutant alleles.

In some embodiments, the clamp oligos comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., inhibitory nucleic acids containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). These properties render LNAs especially useful for the methods described herein.

The LNA clamp oligos can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is identical to a region in the target gene (e.g., to the wild type sequence). The LNA clamp oligos can be chemically synthesized using methods known in the art.

The LNA clamp oligos can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the sequence of the LNA clamp oligos; for example, a series of inhibitory nucleic acids of 10-30 nucleotides spanning the length of a target sequence can be prepared, followed by testing for activity. Optionally, gaps, e.g., of 5-10 nucleotides or more, can be left between the LNA clamp oligos to reduce the number of inhibitory nucleic acids synthesized and tested. GC content is preferably between about 30-60%. General guidelines for designing LNA clamp oligos are known in the art; for example, LNA sequences will bind very tightly to other LNA sequences, so it is preferable to avoid significant complementarity within an LNA. Contiguous runs of more than four LNA residues should be avoided where possible (for example, it may not be possible with very short (e.g., about 9-10 nt) inhibitory nucleic acids). In some embodiments, the LNAs are xylo-LNAs. (see, e.g., You et al., Nucleic Acids Research, 2006, Vol. 34, No. 8 e60).

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); You et al., Nucleic Acids Research, 2006, Vol. 34, No. 8 e60; Ponting et al., Cell 136(4):629-641 (2009), and references cited therein.

Two-Step Clamped PCR

As shown in FIG. 2, in the first round of PCR ("PCR1"), the forward gene-specific primer, which is in cis with (hybridizes to the same strand as) the clamping LNA sequence is used for single strand primer extension. The gene-specific primer also contains a hemi-functional NGS adapter payload. Following purification, e.g., using solid-phase reversible immobilization (SPRI) bead-based cleanup, of the PCR1 product, a second round of PCR ("PCR2") is completed using a first universal primer complementary to a portion of the adapter payload and a paired gene specific reverse primer on the opposite strand containing another hemi-functional NGS adapter payload. A second universal primer identical to the adapter payload on the reverse primer is used to complete amplification of fully indexed amplicons. The use of the second universal primer allows the use of many different NS (e.g., Illumina) adapter sequences with the same single gene specific primers. Alternatively, the reverse primer can include a fully functional NGS primer; this requires the synthesis of numerous fully functional reverse sequences that have different adapter sequences on them. This is more costly and can limits the number of samples that can be run at any given time.

Sequencing

As used herein, "sequencing" includes any method of determining the sequence of a nucleic acid. Any method of sequencing can be used in the present methods, including chain terminator (Sanger) sequencing and dye terminator sequencing. In preferred embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel; see, e.g., US 20140162897, as well as Voelkerding et al., Clinical Chem., 55: 641-658, 2009; and MacLean et al., Nature Rev. Microbiol., 7: 287-296 (2009). Some NGS methods require template amplification and some do not. Amplification-requiring methods include pyrosequencing (see, e.g., U.S. Pat. Nos. 6,210,89 and 6,258,568; commercialized by Roche); the Solexa/Illumina platform (see, e.g., U.S. Pat. Nos. 6,833,246, 7,115,400, and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503). See, e.g., US 20130274147; US20140038831; Metzker, Nat Rev Genet 11(1): 31-46 (2010).

Alternatively, hybridization-based sequence methods or other high-throughput methods can also be used, e.g., microarray analysis, NANOSTRING, ILLUMINA, or other sequencing platforms.

ESR1 and PIK3CA Mutation Analysis Using Enrich-Seq

Approximately 70% of breast cancers are estrogen receptor a (ER) positive and are treated with endocrine therapies. Mutations in the LBD of ESR1 have been shown to be associated with the development of resistance to endocrine therapies. See, e.g., Jeselsohn et al., Nat Rev Clin Oncol. 2015 October; 12(10):573-83; Li et al., Cell Rep. 2013 Sep. 26; 4(6): 10.1016. Mutations in PIK3CA have been associated with non-response to trastuzumab and/or lapatinib (see, e.g., Majewski et al., J Clin Oncol 2015; 33(12):1334-1339. The present methods can be used, e.g., to detect breast cancer-associated mutations, e.g., in double stranded DNA from circulating tumor cells (CTCs), circulating tumor DNA (ctDNA), or exosomes, from subjects (e.g., human subjects) who have been diagnosed with or are suspected of having cancer, e.g., breast cancer. For example, the methods can be used for detecting mutations in the ligand binding domain (LBD) of ESR1, or exon 9 or 20 of PIK3CA in subjects who have or are suspected of having breast cancer.

Exemplary gene-specific primers and LNA clamps useful in these methods are shown herein, for detecting mutations in PIK3CA Exon 9 wild type sequence: TCTCCTG-CTCAGTGATTTCA (SEQ ID NO:8); PIK3CA Exon 20 wild type sequence: TGCACATCATGGTGGCTGGA (SEQ ID NO:9); or ESR1 wild type sequence TGCCCCTC-TATGACCTGCTG (SEQ ID NO:1). The methods can include obtaining a sample comprising CTCs or ctDNA from a subject and using a two-step clamped PCR method as described herein to detect mutations. Preferably, the method includes detecting mutations in ESR1 and/or PIK3CA and is performed in a single undivided reaction, i.e., in a single tube.

Upon detection of one or more mutations in ESR1 (e.g., V534E (1601T>A), P535H (1604C>A), L536R/P/Q (1607T>G/1607T>C/1607TC>AG), Y537N/C/S (1609T>A/1610A>G/1610A>C), or D538G (1613A>G)) the methods can include identifying the subject as having or at risk of developing estrogen receptor (ER)-positive breast cancer that is resistant to endocrine therapy. Endocrine therapies include estrogen-receptor modulators (SERMs), such as tamoxifen and raloxifene; LH blockers such as goserelin (Zoladex); aromatase inhibitors (e.g., anastrozole (Arimidex), exemestane (Aromasin), or letrozole (Femara)); GnRH agonists; and ER degraders (e.g., fulvestrant (Faslodex)) see, e.g., Lumachi et al., Curr Med Chem. 2011; 18(4):513-22; Burstein et al., J Clin Oncol 2014; 32(21):2255-2269. Once endocrine resistance is identified by the detection of an ESR1 mutation, therapeutic options can include treating the subject with chemotherapy or endocrine therapy plus molecular-targeted therapy such as everolimus (Afinitor) or palbociclib (Ibrance). The methods can also include predicting response to treatment with endocrine therapy including investigational agents such as next generation estrogen receptor degraders, combination therapy using endocrine therapy plus histone deacetylase inhibitors, PI3K pathway inhibitors, or androgen receptor blockers.

Upon detection of one or more mutations in PIK3CA (e.g., E542K (c.1624G→A), E545K/Q/G/V (c.1633G→A/1633G>C/1634A>G/1634A>T) in exon 9 and/or H1047R (c.3140A→G), H1047L (c.3140A→T)), the methods can include identifying the subject as having or at risk of developing estrogen receptor (ER)-positive breast cancer that does not respond to trastuzumab and/or lapatinib. The methods can include treating the subject with a therapy that does not include trastuzumab and/or lapatinib. The methods can also include predicting response to investigational therapy with PI3K/AKT pathway inhibitors.

EXAMPLES

The invention is further described in the following examples, which do not limit the scope of the invention described in the claims.

Methods

The following methods were used in the Examples set forth below.

Genomic DNA (gDNA) from circulating tumor cells (CTC) or circulating tumor DNA (ctDNA) was extracted using the Qiagen AllPrep DNA/RNA Micro Kit or the Qiagen Circulating Nucleic Acid Kit, respectively, according to the manufacturer's protocol. A hemi-functional sequencing library was prepared by combining DNA template with new hemi-functional gene-specific primers, matching gene-specific LNA clamp and KAPA HiFi Hot Start PCR Kit (Kapa Biosystems) and performing 25 rounds of primer extension, which represent the critical steps for mutant enrichment.

A 0.4× Solid-phase reversible immobilization (SPRI) bead cleanup was next performed with Agencourt Ampure XP beads (Beckman Coulter) according to manufacturer's protocol with a modified 20 minute incubation and eluted with 31.5 uL nuclease free water. The library was then made fully competent for sequencing by performing an additional 30 cycles of PCR amplification with complementary hemi-functional gene-specific primers, sequencing adapters, and KAPA HiFi Hot Start PCR Kit (Kapa Biosystems). A 0.6×SPRI bead cleanup was next performed with Agencourt Ampure XP beads (Beckman Coulter) according to manufacturer's protocol. The resulting fully functionalized libraries were quantitated using a KAPA Library Quantification Kit (Kapa Biosystems) and processed for Illumina sequencing using an Illumina paired end sequencing method. Raw FASTA sequencing data was de-multiplexed to separate sample data. Individual sample data was processed to generate paired end consensus reads. Complete matching of paired end reads using a FLASH open-source tool was required. Paired consensus reads were then aligned to a human reference genome using the BWA-MEM open-source tool. Resulting alignments were reviewed in the Integrated Genomics Viewer (IGV) and/or called for variance using SAMtools and VarScan tools.

Hemi-Functional Gene Specific Primers

The hemi-functional gene specific primers in this example were designed to accommodate sequencing on the Illumina platform. The following fusion primers were used with the Illumina adaptor sequence shown in italics, the "hinge" phase sequence (so called because it lies between the Illumina adapter payload and the gene-specific portion of the primer) shown as a bold N, and the gene-specific portion of the primer shown in plain text.

| Primer | Sequence | SEQ ID NO: |
|---|---|---|
| PIK3CA exon 9 Forward primer | CCTCTCTATGGGCAGTCGGTGATNGG GAAAATGACAAAGAACAGCTCA | 3 |
| PIK3CA Exon 9 Reverse primer | TCTTTCCCTACACGACGCTCTTCCGAT CTNTCCATTTTAGCACTTACCTGTG\*A\*C | 2 |
| PIK3CA Exon 20 Forward primer | TCTTTCCCTACACGACGCTCTTCCGAT CTNACCCTAGCCTTAGATAAAACTG AGCA | 4 |
| PIK3CA Exon 20 Reverse primer | CCTCTCTATGGGCAGTCGGTGATNTG CATGCTGTTTAATTGTGTGGAAG | 5 |
| ESR1 Exon 8 Forward primer | TCTTTCCCTACACGACGCTCTTCCGAT CTNTCCCACCTACAGTAACAAAGGC ATGG | 6 |
| ESR1 Exon 8 Reverse primer | CCTCTCTATGGGCAGTCGGTGATNGG CTAGTGGGCGCATGTAGGC | 7 |

LNA Clamp Primers
In the present examples, the following LNAs were used:

| Primer | Sequence | SEQ ID NO: |
|---|---|---|
| TKS_PIK3CA Exon 9 LNA | 5'-TCTCCTGC + T + C + A + G + T + GAT + T + T + C + A +/3invdT/-3' | 84 |
| TKS_PIK3CA Exon 20 LNA | 5'-T + G + C + A + C + A + T + C + A + T + GGTGGCTGGA/ 3invdT/-3' | 85 |
| TKS_ESR1 LNA | T + GCC + CCT + C + T + A + T + G + A + C + CTGCTG/ 3InvdT/ | 86 |

Nucleotides followed by a plus (+) sign indicate the locked nucleotides.

Illumina Mi-Seq NGS Universal Hemi-Functional Primers

| No. | Sequence | SEQ ID NO. |
|---|---|---|
| MI-A49 | AATGATACGGCGACCACCGAGATCTACACCGTAGGTA (N1:25252525) (N1) (N2:50000050) (N1) (N1) (N2) (N1) (N1) ACACTCTTTCCCTACACGACGCTCTTCCGATC\*T | 10 |
| MI-A50 | AATGATACGGCGACCACCGAGATCTACACAGCTAGCG (N1:25252525) (N1) (N2:50000050) (N1) (N1) (N2) (N1) (N1) ACACTCTTTCCCTACACGACGCTCTTCCGATC\*T | 11 |
| MI-A51 | AATGATACGGCGACCACCGAGATCTACACTCCTGTGC (N1:25252525) (N1) (N2:50000050) (N1) (N1) (N2) (N1) (N1) ACACTCTTTCCCTACACGACGCTCTTCCGATC\*T | 12 |
| MI-A52 | AATGATACGGCGACCACCGAGATCTACACGTAATCTG (N1:25252525) (N1) (N2:50000050) (N1) (N1) (N2) (N1) (N1) ACACTCTTTCCCTACACGACGCTCTTCCGATC\*T | 13 |
| MI-A53 | AATGATACGGCGACCACCGAGATCTACACAACGTAGG (N1:25252525) (N1) (N2:50000050) (N1) (N1) (N2) (N1) (N1) ACACTCTTTCCCTACACGACGCTCTTCCGATC\*T | 14 |
| MI-A54 | AATGATACGGCGACCACCGAGATCTACACTTCCTGTT (N1:25252525) (N1) (N2:50000050) (N1) (N1) (N2) (N1) (N1) ACACTCTTTCCCTACACGACGCTCTTCCGATC\*T | 15 |
| MI-A55 | AATGATACGGCGACCACCGAGATCTACACTGTCCAGT (N1:25252525) (N1) (N2:50000050) (N1) (N1) (N2) (N1) (N1) ACACTCTTTCCCTACACGACGCTCTTCCGATC\*T | 16 |
| MI-A56 | AATGATACGGCGACCACCGAGATCTACACACAAGGCA (N1:25252525) (N1) (N2:50000050) (N1) (N1) (N2) (N1) (N1) ACACTCTTTCCCTACACGACGCTCTTCCGATC\*T | 17 |
| MI-A57 | AATGATACGGCGACCACCGAGATCTACACCCTTGACC (N1:25252525) (N1) (N2:50000050) (N1) (N1) (N2) (N1) (N1) ACACTCTTTCCCTACACGACGCTCTTCCGATC\*T | 18 |

-continued

| No. | Sequence | SEQ ID NO. |
|---|---|---|
| MI-A58 | AATGATACGGCGACCACCGAGATCTACACCGCTTGTG (N1:25252525) (N1) (N2:50000050) (N1) (N1) (N2) (N1) (N1) ACACTCTTTCCCTACACGACGCTCTTCCGATC*T | 19 |
| MI-A59 | AATGATACGGCGACCACCGAGATCTACACTCCAAGCG (N1:25252525) (N1) (N2:50000050) (N1) (N1) (N2) (N1) (N1) ACACTCTTTCCCTACACGACGCTCTTCCGATC*T | 20 |
| MI-A60 | AATGATACGGCGACCACCGAGATCTACACCTAGTGAC (N1:25252525) (N1) (N2:50000050) (N1) (N1) (N2) (N1) (N1) ACACTCTTTCCCTACACGACGCTCTTCCGATC*T | 21 |
| MI-A61 | AATGATACGGCGACCACCGAGATCTACACAGAACCGT (N1:25252525) (N1) (N2:50000050) (N1) (N1) (N2) (N1) (N1) ACACTCTTTCCCTACACGACGCTCTTCCGATC*T | 22 |
| MI-A62 | AATGATACGGCGACCACCGAGATCTACACTAATTGCA (N1:25252525) (N1) (N2:50000050) (N1) (N1) (N2) (N1) (N1) ACACTCTTTCCCTACACGACGCTCTTCCGATC*T | 23 |
| MI-A63 | AATGATACGGCGACCACCGAGATCTACACCTAGTACA (N1:25252525) (N1) (N2:50000050) (N1) (N1) (N2) (N1) (N1) ACACTCTTTCCCTACACGACGCTCTTCCGATC*T | 24 |
| MI-A64 | AATGATACGGCGACCACCGAGATCTACACGCTATATC (N1:25252525) (N1) (N2:50000050) (N1) (N1) (N2) (N1) (N1) ACACTCTTTCCCTACACGACGCTCTTCCGATC*T | 25 |
| MI-A65 | AATGATACGGCGACCACCGAGATCTACACCAATCGGC (N1:25252525) (N1) (N2:50000050) (N1) (N1) (N2) (N1) (N1) ACACTCTTTCCCTACACGACGCTCTTCCGATC*T | 26 |
| MI-A66 | AATGATACGGCGACCACCGAGATCTACACCGATATCA (N1:25252525) (N1) (N2:50000050) (N1) (N1) (N2) (N1) (N1) ACACTCTTTCCCTACACGACGCTCTTCCGATC*T | 27 |
| MI-A67 | AATGATACGGCGACCACCGAGATCTACACCAGTCAGG (N1:25252525) (N1) (N2:50000050) (N1) (N1) (N2) (N1) (N1) ACACTCTTTCCCTACACGACGCTCTTCCGATC*T | 28 |
| MI-A68 | AATGATACGGCGACCACCGAGATCTACACTAATAAT (N1:25252525) (N1) (N2:50000050) (N1) (N1) (N2) (N1) (N1) ACACTCTTTCCCTACACGACGCTCTTCCGATC*T | 29 |
| MI-A69 | AATGATACGGCGACCACCGAGATCTACACGGAGAGAT (N1:25252525) (N1) (N2:50000050) (N1) (N1) (N2) (N1) (N1) ACACTCTTTCCCTACACGACGCTCTTCCGATC*T | 30 |
| MI-A70 | AATGATACGGCGACCACCGAGATCTACACCTCTCATA (N1:25252525) (N1) (N2:50000050) (N1) (N1) (N2) (N1) (N1) ACACTCTTTCCCTACACGACGCTCTTCCGATC*T | 31 |
| MI-A71 | AATGATACGGCGACCACCGAGATCTACACCAGCGACT (N1:25252525) (N1) (N2:50000050) (N1) (N1) (N2) (N1) (N1) ACACTCTTTCCCTACACGACGCTCTTCCGATC*T | 32 |
| MI-A72 | AATGATACGGCGACCACCGAGATCTACACGGCCAAGG (N1:25252525) (N1) (N2:50000050) (N1) (N1) (N2) (N1) (N1) ACACTCTTTCCCTACACGACGCTCTTCCGATC*T | 33 |
| MI-A73 | AATGATACGGCGACCACCGAGATCTACACGCATATGC (N1:25252525) (N1) (N2:50000050) (N1) (N1) (N2) (N1) (N1) ACACTCTTTCCCTACACGACGCTCTTCCGATC*T | 34 |
| MI-A74 | AATGATACGGCGACCACCGAGATCTACACACTAGGAT (N1:25252525) (N1) (N2:50000050) (N1) (N1) (N2) (N1) (N1) ACACTCTTTCCCTACACGACGCTCTTCCGATC*T | 35 |
| MI-A75 | AATGATACGGCGACCACCGAGATCTACACCCTTACCT (N1:25252525) (N1) (N2:50000050) (N1) (N1) (N2) (N1) (N1) ACACTCTTTCCCTACACGACGCTCTTCCGATC*T | 36 |
| MI-A76 | AATGATACGGCGACCACCGAGATCTACACTGTTGACG (N1:25252525) (N1) (N2:50000050) (N1) (N1) (N2) (N1) (N1) ACACTCTTTCCCTACACGACGCTCTTCCGATC*T | 37 |
| MI-A77 | AATGATACGGCGACCACCGAGATCTACACTACAGTTA (N1:25252525) (N1) (N2:50000050) (N1) (N1) (N2) (N1) (N1) ACACTCTTTCCCTACACGACGCTCTTCCGATC*T | 38 |
| MI-A78 | AATGATACGGCGACCACCGAGATCTACACTTGTTACG (N1:25252525) (N1) (N2:50000050) (N1) (N1) (N2) (N1) (N1) ACACTCTTTCCCTACACGACGCTCTTCCGATC*T | 39 |
| MI-A79 | AATGATACGGCGACCACCGAGATCTACACTCGTGTTG (N1:25252525) (N1) (N2:50000050) (N1) (N1) (N2) (N1) (N1) ACACTCTTTCCCTACACGACGCTCTTCCGATC*T | 40 |
| MI-A80 | AATGATACGGCGACCACCGAGATCTACACAGTCAATG (N1:25252525) (N1) (N2:50000050) (N1) (N1) (N2) (N1) (N1) ACACTCTTTCCCTACACGACGCTCTTCCGATC*T | 41 |
| MI-A81 | AATGATACGGCGACCACCGAGATCTACACTCTGTAGA (N1:25252525) (N1) (N2:50000050) (N1) (N1) (N2) (N1) (N1) ACACTCTTTCCCTACACGACGCTCTTCCGATC*T | 42 |
| MI-A82 | AATGATACGGCGACCACCGAGATCTACACGACAACGA (N1:25252525) (N1) (N2:50000050) (N1) (N1) (N2) (N1) (N1) ACACTCTTTCCCTACACGACGCTCTTCCGATC*T | 43 |
| MI-A83 | AATGATACGGCGACCACCGAGATCTACACCCATGGCT (N1:25252525) (N1) (N2:50000050) (N1) (N1) (N2) (N1) (N1) ACACTCTTTCCCTACACGACGCTCTTCCGATC*T | 44 |

| No. | Sequence | SEQ ID NO. |
|---|---|---|
| MI-A84 | AATGATACGGCGACCACCGAGATCTACACTGACTCTG (N1:25252525) (N1) (N2:50000050) (N1) (N1) (N2) (N1) (N1) ACACTCTTTCCCTACACGACGCTCTTCCGATC*T | 45 |
| MI-A85 | AATGATACGGCGACCACCGAGATCTACACAACGAGGC (N1:25252525) (N1) (N2:50000050) (N1) (N1) (N2) (N1) (N1) ACACTCTTTCCCTACACGACGCTCTTCCGATC*T | 46 |
| MI-A86 | AATGATACGGCGACCACCGAGATCTACACCAGAAGGT (N1:25252525) (N1) (N2:50000050) (N1) (N1) (N2) (N1) (N1) ACACTCTTTCCCTACACGACGCTCTTCCGATC*T | 37 |
| MI-A87 | AATGATACGGCGACCACCGAGATCTACACTGAAGTCA (N1:25252525) (N1) (N2:50000050) (N1) (N1) (N2) (N1) (N1) ACACTCTTTCCCTACACGACGCTCTTCCGATC*T | 38 |
| MI-A88 | AATGATACGGCGACCACCGAGATCTACACATGTTCCT (N1:25252525) (N1) (N2:50000050) (N1) (N1) (N2) (N1) (N1) ACACTCTTTCCCTACACGACGCTCTTCCGATC*T | 39 |
| MI-A89 | AATGATACGGCGACCACCGAGATCTACACAAGTGGCT (N1:25252525) (N1) (N2:50000050) (N1) (N1) (N2) (N1) (N1) ACACTCTTTCCCTACACGACGCTCTTCCGATC*T | 50 |
| MI-A90 | AATGATACGGCGACCACCGAGATCTACACGGTACAAT (N1:25252525) (N1) (N2:50000050) (N1) (N1) (N2) (N1) (N1) ACACTCTTTCCCTACACGACGCTCTTCCGATC*T | 51 |
| MI-A91 | AATGATACGGCGACCACCGAGATCTACACACAAGTGC (N1:25252525) (N1) (N2:50000050) (N1) (N1) (N2) (N1) (N1) ACACTCTTTCCCTACACGACGCTCTTCCGATC*T | 52 |
| MI-A92 | AATGATACGGCGACCACCGAGATCTACACTCACGGTG (N1:25252525) (N1) (N2:50000050) (N1) (N1) (N2) (N1) (N1) ACACTCTTTCCCTACACGACGCTCTTCCGATC*T | 53 |
| MI-A93 | AATGATACGGCGACCACCGAGATCTACACTTGCGTTA (N1:25252525) (N1) (N2:50000050) (N1) (N1) (N2) (N1) (N1) ACACTCTTTCCCTACACGACGCTCTTCCGATC*T | 54 |
| MI-A94 | AATGATACGGCGACCACCGAGATCTACACTTGTAGCC (N1:25252525) (N1) (N2:50000050) (N1) (N1) (N2) (N1) (N1) ACACTCTTTCCCTACACGACGCTCTTCCGATC*T | 55 |
| MI-A95 | AATGATACGGCGACCACCGAGATCTACACTCACCGGA (N1:25252525) (N1) (N2:50000050) (N1) (N1) (N2) (N1) (N1) ACACTCTTTCCCTACACGACGCTCTTCCGATC*T | 56 |
| MI-A96 | AATGATACGGCGACCACCGAGATCTACACCGCGCAAG (N1:25252525) (N1) (N2:50000050) (N1) (N1) (N2) (N1) (N1) ACACTCTTTCCCTACACGACGCTCTTCCGATC*T | 57 |
| P701 | CAAGCAGAAGACGGCATACGAGATTCGCCTTAGTGACTGGAGTCCTCTCTATGGGCAGTCGGTGA | 58 |
| P702 | CAAGCAGAAGACGGCATACGAGATCTAGTACGGTGACTGGAGTCCTCTCTATGGGCAGTCGGTGA | 59 |
| P703 | CAAGCAGAAGACGGCATACGAGATTTCTGCCTGTGACTGGAGTCCTCTCTATGGGCAGTCGGTGA | 60 |
| P704 | CAAGCAGAAGACGGCATACGAGATGCTCAGGAGTGACTGGAGTCCTCTCTATGGGCAGTCGGTGA | 61 |
| P705 | CAAGCAGAAGACGGCATACGAGATAGGAGTCCGTGACTGGAGTCCTCTCTATGGGCAGTCGGTGA | 62 |
| P706 | CAAGCAGAAGACGGCATACGAGATCATGCCTAGTGACTGGAGTCCTCTCTATGGGCAGTCGGTGA | 63 |
| P707 | CAAGCAGAAGACGGCATACGAGATGTAGAGAGGTGACTGGAGTCCTCTCTATGGGCAGTCGGTGA | 64 |
| P708 | CAAGCAGAAGACGGCATACGAGATCCTCTCTGGTGACTGGAGTCCTCTCTATGGGCAGTCGGTGA | 65 |
| P709 | CAAGCAGAAGACGGCATACGAGATAGCGTAGCGTGACTGGAGTCCTCTCTATGGGCAGTCGGTGA | 66 |
| P710 | CAAGCAGAAGACGGCATACGAGATCAGCCTCGGTGACTGGAGTCCTCTCTATGGGCAGTCGGTGA | 67 |
| P711 | CAAGCAGAAGACGGCATACGAGATTGCCTCTTGTGACTGGAGTCCTCTCTATGGGCAGTCGGTGA | 68 |
| P712 | CAAGCAGAAGACGGCATACGAGATTCCTCTACGTGACTGGAGTCCTCTCTATGGGCAGTCGGTGA | 69 |
| P713 | CAAGCAGAAGACGGCATACGAGATAACTTCACGTGACTGGAGTCCTCTCTATGGGCAGTCGGTGA | 70 |
| P714 | CAAGCAGAAGACGGCATACGAGATTGGAGAGGGTGACTGGAGTCCTCTCTATGGGCAGTCGGTGA | 71 |
| P715 | CAAGCAGAAGACGGCATACGAGATACGCATCGGTGACTGGAGTCCTCTCTATGGGCAGTCGGTGA | 72 |
| P716 | CAAGCAGAAGACGGCATACGAGATGTACCGTTGTGACTGGAGTCCTCTCTATGGGCAGTCGGTGA | 73 |
| P717 | CAAGCAGAAGACGGCATACGAGATTACAGTTAGTGACTGGAGTCCTCTCTATGGGCAGTCGGTGA | 74 |
| P718 | CAAGCAGAAGACGGCATACGAGATAATCAACTGTGACTGGAGTCCTCTCTATGGGCAGTCGGTGA | 75 |
| P719 | CAAGCAGAAGACGGCATACGAGATGTACCTAGGTGACTGGAGTCCTCTCTATGGGCAGTCGGTGA | 76 |

-continued

| No. | Sequence | SEQ ID NO. |
|---|---|---|
| P720 | CAAGCAGAAGACGGCATACGAGATCTGGAACAGTGACTGGAGTCCTCTCTATGGGCAGTCGGTGA | 77 |
| P721 | CAAGCAGAAGACGGCATACGAGATGGTGACTAGTGACTGGAGTCCTCTCTATGGGCAGTCGGTGA | 78 |
| P722 | CAAGCAGAAGACGGCATACGAGATGTGCAACCGTGACTGGAGTCCTCTCTATGGGCAGTCGGTGA | 79 |
| P723 | CAAGCAGAAGACGGCATACGAGATGCCTGTCTGTGACTGGAGTCCTCTCTATGGGCAGTCGGTGA | 80 |
| P724 | CAAGCAGAAGACGGCATACGAGATACTGATGGGTGACTGGAGTCCTCTCTATGGGCAGTCGGTGA | 81 |

AATGATACGGCGACCACCGA: P5 sequence (SEQ ID NO: 82) (N1:25252525)(N1)(N2:50000050)(N1)(N1)(N2)(N1)(N1): eight nucleotide randomer (molecular barcode) (N1 = N and N2 = W)

Example 1. ESR1 and PIK3CA Mutation Analysis Using Enrich-Seq

This example describes the development and an exemplary implementation of an approach, described herein as Enrich-Seq, that enlists mutant enrichment using a locked-nucleic acid clamp in combination with a novel technique for library preparation that can accommodate a wide range of input DNA. A highly stringent, multi-phase bioinformatics approach is then applied to ensure optimal specificity of mutation calling.

For the development of the technique we first focused on estrogen receptor (ER)-positive breast cancer, where recurrent mutations in the estrogen receptor alpha gene, ESR1, have recently been detected and appear to confer resistance to endocrine therapy (1-5). The identification of SSRI mutations through non-invasive monitoring of women with metastatic breast cancer who are receiving endocrine therapy may permit the early identification of treatment resistance, allowing timely alterations in therapy. As mutations in ESR1 appear to cluster in the ligand binding domain (LBD), we designed a locked nucleic acid (LNA)-containing oligonucleotide that avidly hybridizes to wild-type ESR1 sequences spanning the most mutated sites in the ESR1 LBD (FIG. 1). This LNA clamp takes advantage of the differential hybridization to perfectly matched wild-type ESR1 sequences and mismatched mutated sequences to allow discrimination of the mutated alleles and thus enriched amplification of mutant DNA templates. We optimized the annealing temperature of this ESR1 clamp to permit the greatest mismatch discrimination between hybridization to wild-type and nine different ESR1 mutant alleles, producing a highly efficient multiplexed assay design framework.

Following optimization of ESR1 LNA design, we proceeded to combine the LNA-based enrichment chemistry with next-generation sequencing (NGS) library preparation methods to further improve specificity and sensitivity of the assay. To optimize the assay to ultra-low sensitivity, we avoided the technical uncertainties of mutant template dilution series or statistical methods to estimate sensitivity and employed a method whereby variant allele fractions could be ascertained definitively during testing. We took advantage of a unique lab resource—a CTC-derived cell line harboring the ESR1 LBD mutation, Y537S (5). Individual cells from this cell line were isolated using micromanipulation and subsequently placed in a background of normal white blood cells to definitively reflect a goal allele fraction for technical optimization. For example, a single cell from this cell line, which has a single mutated ESR1 Y537S allele (heterozygous), placed in a background of 15,000 white blood cells, reflects a mutant allele fraction of 0.01%.

Figure 4:
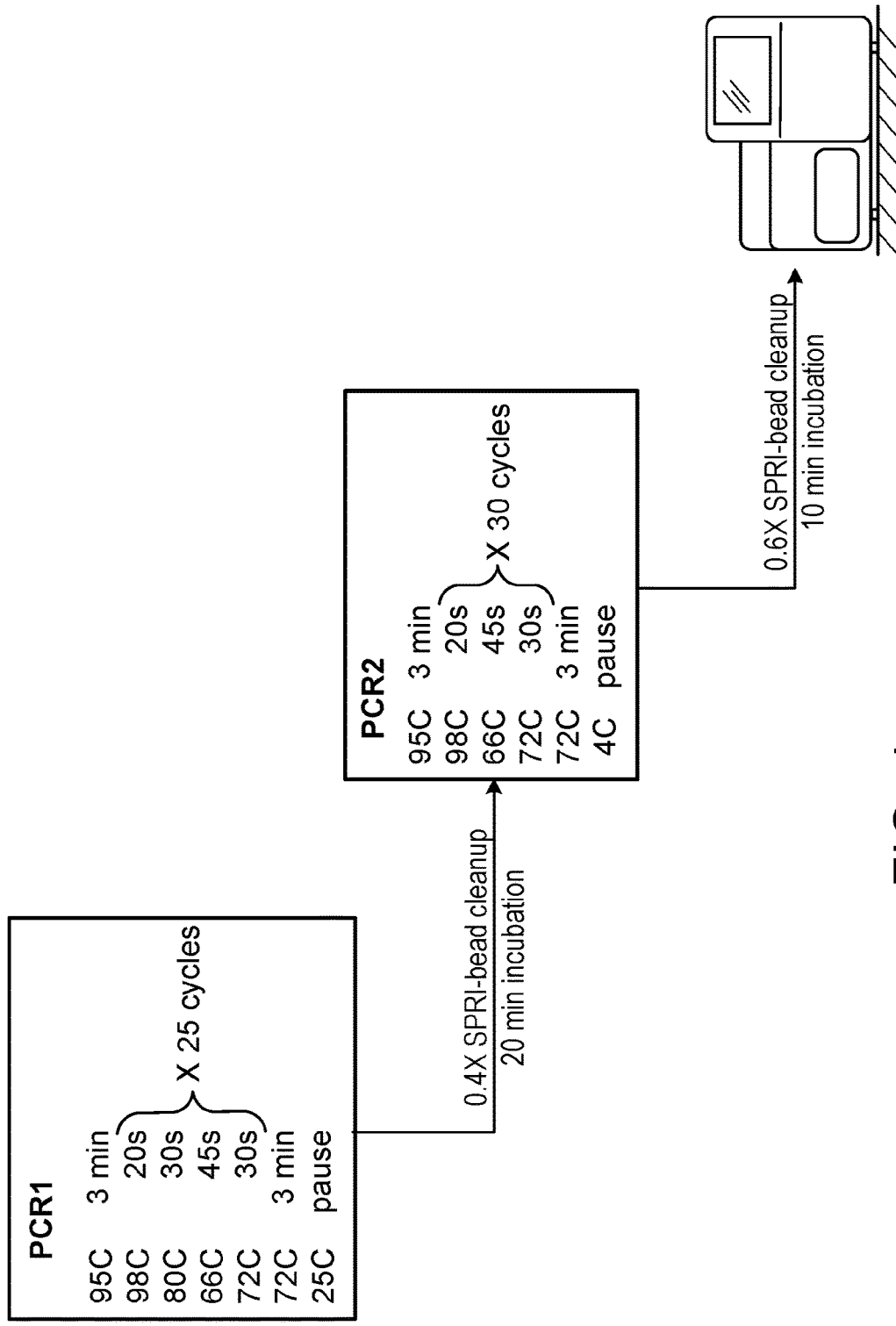
FIG. 4. NGS library preparation PCR conditions. PCR1 includes 25 cycles of primer extension with a lead-in LNA clamp annealing step at 80° C. for 30 seconds. It is followed by a 0.4×SPRI cleanup with an extended incubation. PCR2 is carried out for 30 cycles and is followed by a 0.6× standard SPRI cleanup. Paired end sequencing is done on the Illumina MiSeq platform.

The first component of adaptation of our approach to NGS library preparation was the design of ESR1 amplification primers that flanked the LNA clamp sequence. Optimal primers were chosen using a modified Primer3 algorithm. Gene-specific primers were designed with a hemi-functional sequencing adapter payload as part of a multi-step PCR approach (FIG. 2). Given the low complexity in our allele-specific amplification pool, gene-specific primers were first tested with a phased 3 nucleotide random oligomer (FIG. 3). In the context of enrichment with an LNA clamp, this led to increased non-specific amplification and promiscuous adapter recombinations and thus the oligomers with 3 phased nucleotides were discarded in favor of oligomers with a single phased nucleotide. After finalizing amplification primer design, attention was turned to specific PCR conditions. Annealing and extension temperatures were optimized followed by the addition of a lead-in LNA clamp annealing step in PCR1. Multiple cycle numbers for PCR1 and 2 were next tested. Cycling conditions with the best mutant enrichment balanced with the least likelihood of PCR error introduction were chosen for PCR1 and 2. Solid-phase reversible immobilization (SPRI) bead cleanup conditions following PCR1 and 2 were adjusted by testing numerous SPRI ratios and incubation times to reduce adapter carryover from PCR1 and non-specific amplicons from entering the final library pool after PCR2. The use of a second LNA clamp in PCR2 was evaluated for additional mutant enrichment. Although mutant template enrichment was significantly increased, it occurred at the cost of assay specificity and was eliminated from the protocol. The finalized library preparation PCR conditions are schematized in FIG. 4.

The LNA-enriched library was sequenced using an Illumina paired end sequencing method. Raw FASTA sequencing data was de-multiplexed to separate sample data. Individual sample data was processed to generate paired end consensus reads. Complete matching of paired end reads was performed using a FLASH open-source tool. Paired consensus reads were then aligned to a human reference genome using the BWA-MEM open-source tool. Resulting alignments were reviewed in the Integrated Genomics Viewer (IGV) and/or called for variance using SAMtools and VarScan tools.

Figure 5:
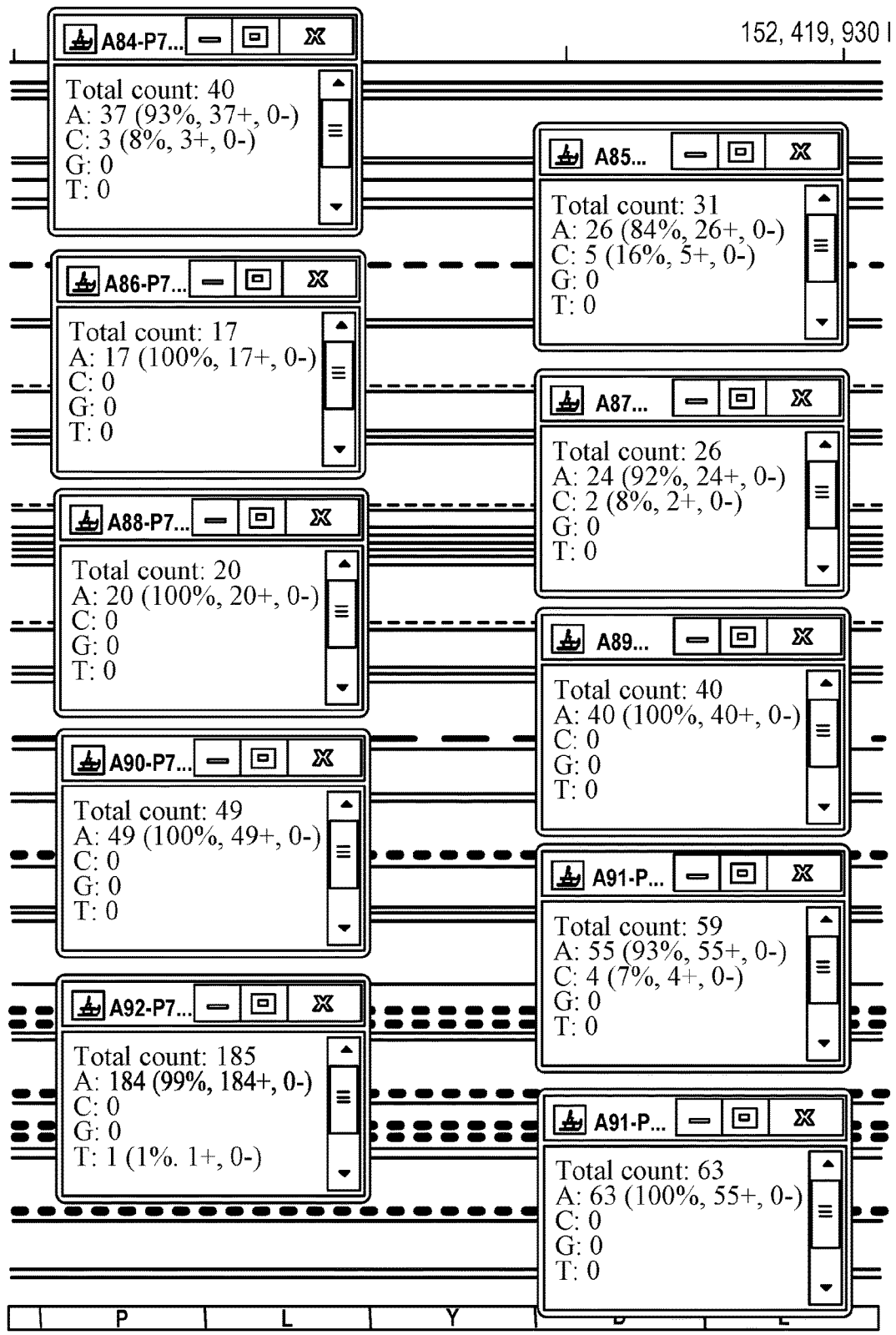
FIG. 5. ESR1 Enrich-Seq genotyping. Example pileups from ESR1 Enrich-Seq genotyping on a test set of 10 replicate samples, each representing 3 cells harboring a heterozygous ESR1 Y537S (A>C substitution) mutation in a background of 15,000 normal white blood cells. The mutation is detected in 4 of the replicates. This demonstrates a sensitivity of 40% at an allele fraction of $1\times10^{-4}$.

Following the extensive optimization described above, assay validation was performed using individual cells harboring a relevant ESR1 mutation placed in a background of normal white blood cells as described above. At an allele fraction of 0.01%, above the limit of detection, assay sensitivity was determined to be 40%. Specificity at this same allele fraction is 100% (FIG. 5).

After the optimization and assay validation described above, ESR1 genotyping using Enrich-Seq was undertaken on CTCs isolated from a pilot cohort of 25 women with ER-positive metastatic breast cancer who had disease progression after receiving at least 2 lines of endocrine therapy at the MGH Cancer Center. An ESR1 mutation was detected in 8/25 (32%) patients, and in two patients, synchronous ESR1 mutations were detected (FIG. 6). The detection of multiple ESR1 mutations in the same patient is a unique advantage of blood-based genotyping that has not been reported in any publication of standard tissue-based ESR1 genotyping, and may have clinical implications for the extent of endocrine resistance that remains to be explored.

As described above, Enrich-Seq remains the only multiplexed ESR1 genotyping assay validated to detect a single variant allele in a background of 10,000 wild-type alleles by combining LNA-based mutant enrichment and next-generation library preparation chemistry. Furthermore, it is the only ESR1 genotyping assay that, to our knowledge, has been validated for use in CTC genotyping; this is particularly relevant as CTC enumeration using the CellSearch platform, for example, is an FDA-approved diagnostic test for prognostication in women with metastatic breast cancer.

REFERENCES

1. Toy W, Shen Y, Won H, Green B, Sakr R A, Will M, et al. ESR1 ligand-binding domain mutations in hormone-resistant breast cancer. Nature genetics 2013; 45:1439-45.
2. Robinson D R, Wu Y M, Vats P, Su F, Lonigro R J, Cao X, et al. Activating ESR1 mutations in hormone-resistant metastatic breast cancer. Nature genetics 2013; 45:1446-51.
3. Li S, Shen D, Shao J, Crowder R, Liu W, Prat A, et al. Endocrine-therapy-resistant ESR1 variants revealed by genomic characterization of breast-cancer-derived xenografts. Cell reports 2013; 4:1116-30.
4. Jeselsohn R, Yelensky R, Buchwalter G, Frampton G, Meric-Bernstam F, Gonzalez-Angulo A M, et al. Emergence of constitutively active estrogen receptor-alpha mutations in pretreated advanced estrogen receptor-positive breast cancer. Clinical cancer research: an official journal of the American Association for Cancer Research 2014; 20:1757-67.
5. Yu M, Bardia A, Aceto N, Bersani F, Madden M W, Donaldson M C, et al. Cancer therapy. Ex vivo culture of circulating breast tumor cells for individualized testing of drug susceptibility. Science 2014; 345:216-20.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
providing a sample comprising a dsDNA;
contacting the sample with primers consisting of:
- a forward gene-specific primer comprising a first hemi-functional Next Generation Sequencing (NGS) adapter sequence, and
- a clamping oligonucleotide that optionally comprises one or more locked nucleotides, wherein the forward primer and clamping oligonucleotide are in cis, and wherein the clamping oligo hybridizes to a wild type sequence of the target gene in a region suspected of comprising one or more mutations;

performing a first round of single strand primer extension PCR, to produce a first population of amplicons;
optionally purifying the first population of amplicons;
contacting the first population of amplicons with a mixture comprising:
- a first universal primer complementary to a portion of the first hemi-functional NGS adapter sequence on the amplicons, wherein amplification with the primer creates a first fully functional NGS adapter sequence,
- a reverse gene specific primer comprising a second hemi-functional NGS adapter sequence on the amplicons, wherein the reverse primer is in trans with the primer complementary to a portion of the first NGS adapter sequence, and;
- a second universal primer identical to the second hemi-functional NGS adapter sequence on the reverse primer, wherein amplification with the second universal primer creates a second fully functional NGS adapter sequence;

performing a second round of PCR to complete amplification of a second population of amplicons comprising both first and second fully functional NGS adapter sequences; and
sequencing the second population of amplicons.

2. The method of claim 1, wherein the dsDNA is or comprises genomic DNA.

3. The method of claim 1, wherein the dsDNA is from circulating tumor DNA (ctDNA), in plasma or urine, circulating tumor cells (CTCs), or exosomes.

4. The method of claim 1, wherein purifying the first population of amplicons comprises using solid-phase reversible immobilization (SPRI) bead-based cleanup.

5. The method of claim 1, wherein the target sequence is in the estrogen receptor 1 (ESR1), preferably in the ligand binding domain.

6. The method of claim 5, wherein the target sequence comprises ESR1 wild type sequence TGCCCCTCTATGACCTGCTG (SEQ ID NO:1).

7. The method of claim 5, wherein the sample is from a subject suspected of having receptor (ER)-positive breast cancer, the method further comprising comparing the sequences of the second population of amplicons to a reference wild type target sequence to thereby detect mutations in the target sequence;
selecting a subject who has a mutation in ESR1; and
administering a chemotherapy for breast cancer that does not include endocrine therapy to the selected subject who has a mutation in ESR1.

8. The method of claim 5, wherein the sample is from a subject suspected of having receptor (ER)-positive breast cancer, the method further comprising comparing the sequences of the second population of amplicons to a reference wild type target sequence to thereby detect mutations in the target sequence;
selecting a subject who does not have a mutation in ESR1; and
administering endocrine therapy to the selected subject who has been identified as not having a mutation in ESR1.

9. The method of claim 1, wherein the target sequence is in phosphatidylinositol-4,5-bisphosphate 3-kinase, catalytic subunit alpha (PIK3CA), optionally in exons 9 and/or 20.

10. The method of claim 9, wherein the target sequence comprises PIK3CA Exon 9 wild type sequence: TCTCCTGCTCAGTGATTTCA (SEQ ID NO:8) or PIK3CA Exon 20 wild type sequence: TGCACATCATGGTGGCTGGA (SEQ ID NO:9).

11. The method of claim 9, wherein the sample is from a subject suspected of having receptor (ER)-positive breast cancer, the method further comprising comparing the sequences of the second population of amplicons to a reference wild type target sequence to thereby detect mutations in the target sequence;
selecting a subject who has a mutation in PIK3CA; and
administering a chemotherapy for breast cancer that does not include trastuzumab and/or lapatinib to the selected subject who has been identified as having a mutation in PIK3CA.

12. The method of claim 9, wherein the sample is from a subject suspected of having receptor (ER)-positive breast cancer, the method further comprising comparing the sequences of the second population of amplicons to a reference wild type target sequence to thereby detect mutations in the target sequence;
selecting a subject who does not have a mutation in PIK3CA; and
administering trastuzumab and/or lapatinib to the selected subject who has been identified as not having a mutation in PIK3CA.

* * * * *